: US005639935A

United States Patent [19]
Cooper et al.

[11] Patent Number: 5,639,935
[45] Date of Patent: Jun. 17, 1997

[54] PROCESS FOR RECOVERING OLEFINS FROM GASEOUS MIXTURES

[75] Inventors: Jeremy Bernard Cooper, West Sussex; Karen Small, Scotland, both of United Kingdom

[73] Assignee: BP Chemicals Limited, London, England

[21] Appl. No.: 524,525

[22] Filed: Sep. 7, 1995

[30] Foreign Application Priority Data

Oct. 4, 1994 [GB] United Kingdom ............... 9419963

[51] Int. Cl.$^6$ .............................. C07C 7/148; C07C 7/10
[52] U.S. Cl. ........................ 585/845; 585/848; 585/833
[58] Field of Search .................... 585/845, 846, 585/848, 833

[56] References Cited

U.S. PATENT DOCUMENTS

| 2,245,719 | 6/1941 | Robey ........................... 95/172 |
| 3,755,487 | 8/1973 | Jahnig et al. ................... 585/848 |
| 3,868,398 | 2/1975 | Kroll et al. .................... 260/438.1 |

FOREIGN PATENT DOCUMENTS

| 038077 | 10/1981 | European Pat. Off. ......... C07C 7/156 |
| 2296643 | 7/1976 | France ......................... C07F 5/00 |
| 428106 | 5/1935 | United Kingdom . |

OTHER PUBLICATIONS

"Mono–Olefins, Chemistry and Technology"; F. Asinger; Pergamon Press; pp. 256–259, ©1968. (No Month).
"Base Stock From Petroleum and Natural Gas for the Chemical Industry"; Sixth World Petroleum Congress Proceedings; Frankfurst/Main, Jun. 19–26, 1963; Section IV, pp. 325–343.

Primary Examiner—Glenn A. Caldarola
Assistant Examiner—In Suk Bullock
Attorney, Agent, or Firm—Fay, Sharpe, Beall, Fagan, Minnich & McKee

[57] ABSTRACT

Ethylene and propylene are recovered from a mixture thereof with other hydrocarbons by: (a) feeding the mixture to a separation zone with a top and a bottom; (b) feeding to the top above the mixture an aqueous complexing solution to form Cu(I) complexes of ethylene and propylene; (c) feeding below the mixture ethylene to strip propylene from the propylene complex; (d) removing from the bottom below the stripping gas a first liquid stream containing the Cu (I) ethylene complex; (e) recovering ethylene from the Cu(I) complex using reduced pressure and/or elevated temperature; (f) removing from the separation zone between the the gaseous mixture and the complexing solution, a second liquid stream comprising Cu (I) propylene complex; (g) recovering propylene from the Cu(I) complex and producing a liquid recycle stream comprising copper (I) salt; and (h) recycling the liquid recycle stream from step (g) to the separation zone.

14 Claims, 1 Drawing Sheet

PROCESS FOR RECOVERING OLEFINS FROM GASEOUS MIXTURES

BACKGROUND OF THE INVENTION

1. Field of the Invention

The present invention relates to a process for recovering olefins from gaseous mixtures and, in particular, relates to the recovery of ethylene and propylene from a gaseous mixture comprising ethylene, propylene, saturated hydrocarbons and optionally other olefins.

2. Description of the Related Art

The selective absorption of ethylene in copper salt solutions is described by F Asinger (translated by B J Mazzard) in Mono-olefins, Chemistry and Technology, Pergamon Press, 1968, at pages 256 to 259. This also compares the solubility of ethylene with the solubilities of other olefins such as propylene in copper (I) chloride-ethanolamine solutions. A process for the separation of ethylene from the dehydrogenation products of ethane is described. This process is the subject of GB 428,106.

U.S. Pat. No. 2,245,719 relates to absorption of lower olefins (ethylene, propylene and butylenes) from gaseous mixtures containing the olefins and saturated hydrocarbons by contacting the gaseous mixture with cool solutions of cuprous is salts and liquid organic nitrogen compounds such as pyridine, piperidine, formamide and acetamide, preferably pyridine. The solubility of the saturated hydrocarbons and hydrogen is low in this absorbent solution. A substantially pure ethylene gas is said to be obtainable from the olefin saturated absorption solution by partially releasing the pressure or slightly heating to first evolve the propylene with a small amount of ethylene, after which an ethylene-rich gas can be obtained on further heating or lowering of the pressure.

EP 0038077 relates to a process in which a monoolefin can be separated from another monoolefin by contacting a mixture of the olefins with a complexing agent selected from cuprous salts of sulfonic acids or dialkyl phosphates dissolved in a suitable hydrocarbon solvent under conditions such that the monoolefins form complexes of different strengths with the complexing agent. The use of a suitable hydrocarbon solvent is said to be critical and aqueous solutions of cuprous salts are said to lack stability and be generally unsuitable for forming the complexing agent. According to EP 0038077 any monoolefin can be separated from another monoolefin so long as the two monoolefins form complexes of different strengths with the complexing agent. In particular, isomers of butene or isomers of pentene are said to be separable. It is said to be more difficult to separate isomers of hexene or heavier olefins. Table I of EP 0038077 sets forth the equilibrium constants (K values) for olefins with a copper (I) dodecylbenzene sulfonate in p-xylene complexing reagent. According to EP 0038077, the Table shows that the process would be very effective in separating cis-butene-2 from trans-butene-2, which have K values of 7.53 and 2.69 respectively. According to EP 0038077, the Table shows that the process would be effective for separating butene-1 from isobutene, which have K values of 6.6 and 4.74 respectively. The separation of propylene from ethylene with K values of 1.72 and 1.31 respectively, is not described in EP 0038077. According to the data in EP 0038077, the K values of ethylene and propylene are quite similar, any difference indicating that propylene forms the stronger complex.

The Proceeding of the Sixth World Petroleum Congress, Frankfurt-amo-Main, June 19–26, Section IV entitled "Base Stocks from Petroleum and Natural Gas For the Chemical Industry" published by Verein zur Forderung des 6. Welt-Erd öl-Kongresses, Hamburg describes in paper 14 the recovery of mono-olefins with the aid of metal salt solutions. Two industrial processes are described; cracked gas separation with ethanolamine copper (I) nitrate solution and recovery of olefins with silver-fluoroborate. According to the paper at pages 340 to 341, copper ethanolamine solution has a lower capacity for propylene than for ethylene so that small amounts of propylene can be removed by stripping the charged solution with ethylene.

There remains a need for a process to recover ethylene and propylene separately from a gaseous mixture comprising ethylene, propylene, saturated hydrocarbons and optionally other olefins.

SUMMARY OF THE INVENTION

According to the present invention there is provided a process for recovering ethylene and propylene from a gaseous mixture comprising ethylene, propylene, saturated hydrocarbons and optionally other olefins which process comprises:

(a) feeding the gaseous mixture to a separation zone comprising in its vertical orientation a top and a bottom;

(b) feeding to the top of the separation zone at a point above the feed point of the gaseous mixture an aqueous complexing solution comprising a copper (I) salt and an aqueous solvent to form copper (I) complexes of ethylene and propylene;

(c) feeding to the separation zone at a point below the feed point of the gaseous mixture a stripping gas comprising ethylene to strip propylene from the copper (I) complex of propylene in the separation zone;

(d) removing from the bottom of the separation zone below the feed point of the stripping gas a first liquid stream comprising complexing solution and copper (I) complex of ethylene;

(e) recovering ethylene from the first liquid stream by subjecting said stream to conditions of reduced pressure and/or elevated temperature;

(f) removing from the separation zone at a point between the feed points of the gaseous mixture and the complexing solution, a second liquid stream comprising complexing solution and copper (I) complex of propylene;

(g) recovering propylene from the second liquid stream by subjecting said stream to conditions of reduced pressure and/or elevated temperature and producing a liquid recycle stream comprising copper (I) salt; and (h) recycling the liquid recycle stream from step (g) to the separation zone.

DESCRIPTION OF THE PREFERRED EMBODIMENTS

Figure 1:
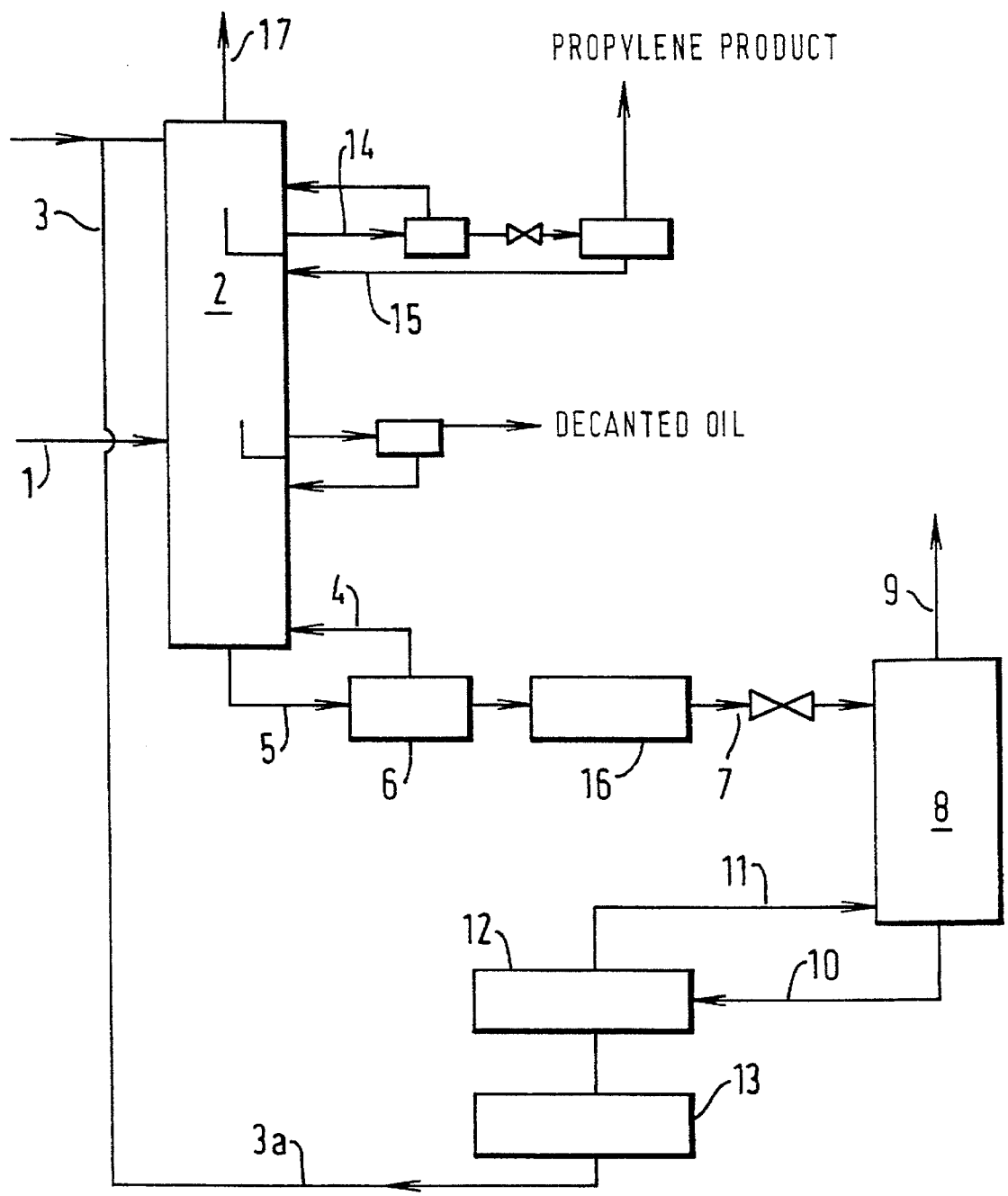
FIG. 1 is a schematic representation of the process.

The feature of the present invention is the so-called absorber/stripper technique. Thus, the present invention uses an aqueous solution of a copper (I) salt which absorbs ethylene and propylene in the gaseous mixture by forming complexes with these olefins in the separation zone. A stripping gas comprising ethylene is then fed to the lower part of the separation zone, below the gaseous mixture feed point and this strips propylene from its complex with copper(I); the copper (I) complex of ethylene passes down the separation zone and is removed as a first liquid stream below the feed point of the stripping gas. Ethylene is more strongly complexed with the copper (I) salt than propylene.

Propylene passes towards the top of the separation zone where it complexes with copper (I) and is removed at a point above the gaseous mixture feed point as a second liquid stream. Ethylene and propylene are separately recovered from the first and second liquid streams by subjecting the streams to conditions of reduced pressure and/or elevated temperature; the recovery of propylene from the second liquid stream leaves behind a liquid stream comprising copper (I) salt which is recycled to the separation zone. A portion of the ethylene recovered from the first liquid stream is suitably recycled to the separation zone as a component of the stripping gas.

The aqueous solvent for the copper (I) salt may comprise water and an organic nitrogen compound such as pyridine, piperidine, hydroxypropionitrile, diethylene triamine, acetonitrile, formamide and acetamide, and derivatives thereof, preferably hydroxypropionitrile or pyridine.

Copper (I) salts which may be used in the process of the present invention include copper (I) acetate, copper (I) nitrate and copper (I) sulphate. The copper (I) salt is suitably copper (I) nitrate.

The molar ratio of copper (I) salt to the nitrogen compound in the aqueous solution for the copper (I) salt is suitably in the range from 1:1 to 1:6, preferably about 1:2. This range is particularly effective when copper (I) nitrate is used with hydroxypropionitrile or pyridine.

The concentration of copper (I) salt in the aqueous complexing solution is preferably at least 0.5 moles of salt per liter of solvent, more preferably at least 2 moles of salt per liter of solvent.

It is desirable to treat the gaseous mixture used in the process of the present invention to remove any acetylenic compounds, for example, by absorption using a zeolite bed containing silver ions, or by selective hydrogenation of the acetylene. The amount of acetylinic hydrocarbons in the gaseous mixture should suitably be reduced to below 20 ppm, preferably below 10 ppm and most preferably below 1 ppm, prior to contact with the complexing solution. This would prevent any inadvertent risk of forming copper acetylide and any danger of explosion associated therewith.

Similarly, any hydrogen sulphide present in the gaseous mixture fed to the separation zone should suitably be removed therefrom in any known manner in order to avoid the risk of poisoning the copper (I) salt.

The gaseous mixture used in the process of the present invention is suitably a cracked gas from which the majority of the C5 and higher hydrocarbons have been removed since these may contaminate the first liquid stream removed from the separation zone. The gaseous mixture may thus comprise ethylene, propylene, butenes, methane, ethane, propane, butane and hydrogen. Small amounts of pentanes and pentenes can be tolerated in the gaseous mixture.

The gaseous mixture used in the process of the present invention may additionally comprise carbon monoxide. Since carbon monoxide complexes more strongly with copper (I) salts than olefins, copper (I) complex of carbon monoxide will be removed together with copper (I) complex of ethylene from the separation zone in the first liquid stream. The carbon monoxide may be separated from the ethylene using an aqueous complexing solution in a manner similar to the absorber/stripper process of the present invention.

The gaseous mixture used in the process of the present invention may additionally comprise butenes. Since n-butene has a similar complexing strength to propylene, copper (I) complex of butene will be removed from the separation zone in the second liquid stream comprising copper (I) complex of propylene. n-Butene and propylene may be separated using conventional non-cryogenic processes.

The gaseous mixture used in the process of the present invention may also comprise water and may optionally be saturated with water.

The separation zone may have any suitable number of theoretical stages, depending upon the composition of the gaseous mixture to be treated, the purity required for the ethylene and propylene products and the nature of the complexing solution used.

The separation zone may be maintained at any suitable pressure, for example about 500 KPa (5 bara).

The separation zone should be maintained at as low a temperature as practicable, preferably without the need for refrigeration, for example about 30° to 35° C.

The complexing solution fed to the separation zone may be controlled to prevent ethylene leaving the separation zone along with the second liquid stream and propylene leaving with the residual gas at the top of the separation zone. Similarly, the stripping gas comprising ethylene fed to the separation zone may be controlled to prevent propylene leaving the separation zone along with the first liquid stream.

In step (e) the first liquid stream removed from the separation zone and comprising copper (I) complex of ethylene is suitably subjected to conditions of temperature and/or pressure to recover at least a portion of the ethylene complexed with copper (I). This ethylene may be fed to the separation zone as the or as a component of the stripping gas.

The first liquid stream is suitably maintained at the same pressure as the separation zone and is suitably heated to an elevated temperature to provide sufficient ethylene gas for the stripping gas, for example heating to about 72° C. at about 500 KPa (5 bara). Feeding ethylene at an elevated temperature in this way performs the function of a reboiler in the separation zone.

Alternatively, ethylene for the stripping gas may be derived from the first liquid stream by reducing the pressure and flashing ethylene off from the stream. The ethylene so derived from the first liquid stream may have to be recompressed to provide the stripping gas.

The first liquid stream, from which optionally part of the ethylene has been recovered to provide the stripping gas, is then introduced, with or without the addition of heat, to a first flash distillation zone to form a gaseous fraction comprising ethylene product and a liquid fraction comprising the copper (I) complexing solution. The liquid fraction from the flash zone is recycled to the separation zone.

The first flash distillation zone may be operated at a pressure below that of the separation zone. The first flash distillation zone is operated to produce at its base a copper (I) complexing solution which is substantially free of ethylene. The copper (I) complexing solution recovered may contain a copper (I) complex of carbon monoxide if the initial gaseous mixture used contained carbon monoxide. Carbon monoxide may be similarly recovered from this first liquid stream by subjecting said stream to conditions of reduced pressure and/or elevated temperature more severe than those in the first flash distillation zone. This will result in a gaseous fraction comprising carbon monoxide and a liquid fraction comprising the copper (I) complexing solution, the liquid fraction being recycled to the separation zone.

The second liquid stream withdrawn from the separation zone comprising copper (I) complex of propylene may also contain dissolved hydrocarbons. These dissolved hydrocarbons, are not chemically bound to the copper (I) salt are therefore more readily displaced from the liquid stream than the complexed propylene.

In step (g), propylene may be recovered from the second liquid stream in a manner similar to the recovery of ethylene from the first liquid stream, ie either by heating the liquid stream or by processing the second liquid stream, with or without the addition of heat, in a second flash distillation zone to form a gaseous fraction comprising propylene and a liquid recycle stream comprising the copper (I) complexing solution.

The recycle liquid stream from the second flash zone is suitably fed to the separation zone at one or more points between the top of the separation zone and the feed point of the gaseous mixture.

The present invention is further illustrated with reference to the accompanying FIG. 1.

A gaseous feed mixture (1) is fed to the separation zone (2). An aqueous complexing solution (3) comprising a copper (I) salt and an aqueous solvent is fed to the top of the separation zone (2) at a point above the feed point of the gaseous mixture (1) to form copper (I) complexes of ethylene and propylene. A stripping gas (4) comprising ethylene is fed to the separation zone (2) below the feed point of the gaseous feed mixture (1). The stripping gas (4) strips propylene from the copper (I)- propylene complex in the separation zone below the feed point of the gaseous mixture (1). A first liquid stream (5) comprising complexing solution and copper (I)-ethylene complex is removed from the bottom of the separation zone (2). The first liquid stream (5) at a temperature of 34° C. is fed to a heater (6) at a temperature of 72° C. which heater (6) is maintained at the same pressure (500 KPa) as the separation zone. A vapour and liquid phase are formed in the heater (6) and the vapour comprising mainly ethylene is withdrawn from the heater at a temperature of 72° C. to provide stripping gas (4) for the separation zone (2). The liquid phase from heater (6) is further heated in heater (16) and is withdrawn as stream (7) from the heater at a temperature of 95° C. and a pressure of 500 KPa. The liquid stream (7) is fed to a flash distillation zone (8) operated at 100 KPa (1 bara) to form a gaseous fraction (9) comprising ethylene product and a liquid fraction (10) comprising the copper (I) complexing solution. The liquid fraction (10) is then fed to a heater (12) where a portion of the liquid fraction is vapourised and is fed as reboil (11) to the bottom of the flash distillation zone (8) at a temperature of 99.4° C. The remainder of the liquid fraction is then fed to a cooler (13) and a copper liquor recycle (3a) is withdrawn from the cooler at a temperature of 30° C. and recycled to the separation zone together with complexing solution (3) and water added to make up for losses in the product gas streams. A second liquid stream (14) comprising the complexing solution and copper (I)-propylene complex is withdrawn from the separation zone (2) at a point between the feed points of the gaseous feed mixture and the complexing solution. Propylene is recovered from the second liquid stream by subjecting this second liquid stream to conditions of reduced pressure and/or elevated temperature to produce a liquid recycle stream (15) comprising copper (I) salt which is recycled to the separation zone (2). Any residual gases (17) are withdrawn from the head of the separation zone.

The feasibility of using selective absorption with an aqueous copper(I) complexing solution to recover ethylene and propylene from cracked gas has been studied using a an XL computer model to quantify the performance of a separation zone.

The process is an equilibrium reaction with the olefins competing with each other to form copper complexes with the copper (I). This was thought to be easier to represent in XL than on ASPEN® but this is less rigorous in representing the physical properties and VLE (vapour-liquid equilibria). Approximate heats of reaction, latent heats and specific heats were used. The process is almost isothermal because of the overwhelming quantity of water needed to dissolve the copper complex (500 grms per mole of copper). Reaction equilibrium data for ethylene and propylene with copper were extrapolated from two experiments at different temperatures. VLE data for non-reacting components were based on pure component vapour pressures regressed on temperature using Antoine's equation. A quasi-immiscible liquid system was then used to calculate component vapour pressures; vapour pressures from the two phases were added. The water vapour pressure was reduced by dilution with the copper (I) salts and complexes on a mole fraction basis. Non-olefinic hydrocarbons were diluted by each other and by 1/1000th part of the water; ideal VLE rules were then applied to this composition.

The computer model calculated the conditions on each tray of the separation zone and adjusted vapour and liquid component flows iteratively to fit VLE and component mass balance on each tray. Tray temperature was adjusted to fit tray heat balance. Considerable effort was necessary to make the calculation converge, including not only heavy damping of most recalculated values but also controller type functions (proportional, integral and derivative) on 'boil up' and 'reflux' and feed forward loops to liquid and vapour flows on each tray.

The model simulated a separation zone fed with copper nitrate/organic nitrogen compound in water (2 moles Cu/liter) at the top and with pretreated (to remove all of hydrogen sulphide and acetylene and most C5's) cracked gas in the middle. The gaseous mixture composition was ethylene (1.2825 mols.), propylene 0.3362 (mols.), hydrogen+methane+ethane 2.4021(mols.) (VLE treated as ethane with an adjustment for water), propane (0.2261 mols), butane (0.059) and pentane (0.0803 mols).

The model simulated an ethylene laden, propylene free, first liquid stream removed from the bottom of the separation zone and a feed of ethylene as stripping gas being about 81% of the ethylene removed in the first liquid stream. The recovered ethylene stream contained less than 0.1% propylene on a dry basis.

A second liquid stream removed from the separation zone above the feed point was flashed to give a propylene product containing only 0.6% ethylene on a dry basis. Olefin loss overhead in residual gas was 0.2% representing 2% of feed propylene. The results of the simulation are shown in the Table below in which the results or vapour and liquid flows for a 20 theoretical stages (trays) separation zone with feed to tray 15 from the top are tabulated. The ethylene stripper gas is shown as being introduced to the base of the separation zone at 71.8° C. and 500 KPa (5 bar). The complexing solution is shown as being introduced to the top of the separation zone at 30° C.

The liquid flow from the bottom (tray 20) containing very little propylene, is fed to a vaporiser where ethylene is recovered for feeding as stripping gas to the separation zone. The remaining liquid is introduced to a first flash distillation zone which has been modelled and these results are also shown in the Table as a 3 theoretical stage (tray) flash distillation with ethylene-free aqueous complexing solution as liquid flow from the base.

| C2H4 RECOVERY | Tray | Temp C. | Vapour Moles per hour | | | | | | | |
|---|---|---|---|---|---|---|---|---|---|---|
| | | | C2H4 | C3H6 | Others | C3H8 | C4H10 | Water | C5H12 | Total |
| COMPLEXING SOLN. IN | | 30 | | | | | | | | |
| FUEL GAS PRODUCT | 1 | 30.0 | 0.000 | 0.006 | 2.383 | 0.220 | 0.044 | 0.023 | 0.011 | 2.69 |
| | 2 | 30.0 | 0.000 | 0.016 | 2.427 | 0.235 | 0.057 | 0.024 | 0.023 | 2.78 |
| | 3 | 30.1 | 0.000 | 0.031 | 2.428 | 0.236 | 0.061 | 0.024 | 0.034 | 2.81 |
| | 4 | 30.1 | 0.000 | 0.053 | 2.429 | 0.236 | 0.063 | 0.024 | 0.047 | 2.85 |
| Total pressure 500 KPa | 5 | 30.1 | 0.000 | 0.087 | 2.429 | 0.237 | 0.064 | 0.025 | 0.061 | 2.90 |
| | 6 | 30.2 | 0.000 | 0.136 | 2.430 | 0.237 | 0.064 | 0.025 | 0.077 | 2.97 |
| | 7 | 30.2 | 0.000 | 0.202 | 2.431 | 0.237 | 0.065 | 0.026 | 0.095 | 3.06 |
| | 8 | 30.2 | 0.000 | 0.286 | 2.431 | 0.237 | 0.065 | 0.027 | 0.116 | 3.16 |
| VAP. IN FROM C3H6 DEGASSING | | 34.4 | 0.000 | 0.016 | 0.047 | 0.017 | 0.013 | 0.002 | 0.096 | 0.19 |
| CRUDE C3H6 PRODUCT at 100 KPa | | 80.0 | 0.002 | 0.329 | 0.002 | 0.000 | 0.008 | 0.287 | 0.031 | 0.66 |
| LIQ. IN FROM C3H6 REGEN. | | 30 | | | | | | | | |
| | 9 | 30.3 | 0.001 | 0.371 | 2.385 | 0.220 | 0.053 | 0.027 | 0.045 | 3.10 |
| | 10 | 30.5 | 0.008 | 0.833 | 2.425 | 0.234 | 0.067 | 0.032 | 0.084 | 3.68 |
| | 11 | 30.7 | 0.035 | 1.236 | 2.421 | 0.233 | 0.068 | 0.036 | 0.110 | 4.14 |
| Total pressure 500 KPa | 12 | 30.9 | 0.125 | 1.481 | 2.417 | 0.231 | 0.067 | 0.040 | 0.122 | 4.48 |
| | 13 | 31.2 | 0.396 | 1.551 | 2.414 | 0.230 | 0.065 | 0.044 | 0.122 | 4.82 |
| | 14 | 31.8 | 1.079 | 1.436 | 2.411 | 0.229 | 0.064 | 0.050 | 0.114 | 5.38 |
| | 15 | 32.3 | 2.326 | 1.145 | 2.407 | 0.228 | 0.062 | 0.061 | 0.098 | 6.33 |
| GASEOUS FEED MIXTURE | | 30.0 | 1.283 | 0.336 | 2.402 | 0.226 | 0.059 | 0.000 | 0.080 | 4.39 |
| | 16 | 33.5 | 2.458 | 0.481 | | | | 0.030 | | 2.97 |
| Total pressure 500 KPa | 17 | 33.7 | 4.868 | 0.316 | | | | 0.053 | | 5.24 |
| | 18 | 33.7 | 5.286 | 0.112 | | | | 0.056 | | 5.45 |
| | 19 | 33.7 | 5.361 | 0.037 | | | | 0.056 | | 5.45 |
| | 20 | 34.2 | 5.416 | 0.012 | | | | 0.058 | | 5.49 |
| C2H4 STRIPPING GAS IN | | 71.8 | 5.334 | 0.003 | | | | 0.354 | | 5.69 |
| | | 95.0 | | | | | | | | |
| ETHYLENE PRODUCT | 1 | 91.8 | 1.278 | 0.000 | 0.000 | 0.000 | 0.000 | 3.471 | 0.000 | 4.75 |
| | 2 | 95.5 | 0.028 | 0.000 | 0.000 | 0.000 | 0.000 | 0.160 | 0.000 | 0.19 |
| Total pressure 100 KPa | 3 | 99.4 | 0.013 | 0.000 | 0.000 | 0.000 | 0.000 | 4.892 | 0.000 | 4.90 |

| Liquid Moles per hour | | | | | | | | | | |
|---|---|---|---|---|---|---|---|---|---|---|
| Tray | Temp C. | Free Cu | C2H4 | C3H6 | Others | C3H8 | C4H10 | Water | C5H12 | Total | |
| | 30 | 13.472 | 0.001 | 0.000 | 0.000 | 0.000 | 0.000 | 374.23 | 0 | 374.2 | |
| 1 | 30.0 | 13.461 | 0.001 | 0.010 | 0.044 | 0.015 | 0.013 | 374.215 | 0.011 | 374.3 | |
| 2 | 30.0 | 13.446 | 0.001 | 0.025 | 0.045 | 0.016 | 0.017 | 374.215 | 0.023 | 374.3 | |
| 3 | 30.1 | 13.423 | 0.001 | 0.047 | 0.046 | 0.016 | 0.019 | 374.216 | 0.036 | 374.4 | |
| 4 | 30.1 | 13.389 | 0.001 | 0.082 | 0.047 | 0.017 | 0.020 | 374.216 | 0.050 | 374.4 | |
| 5 | 30.1 | 13.340 | 0.001 | 0.130 | 0.047 | 0.017 | 0.020 | 374.217 | 0.066 | 374.5 | |
| 6 | 30.2 | 13.274 | 0.001 | 0.197 | 0.048 | 0.017 | 0.021 | 374.218 | 0.084 | 374.6 | |
| 7 | 30.2 | 13.189 | 0.001 | 0.281 | 0.049 | 0.017 | 0.021 | 374.219 | 0.105 | 374.7 | |
| 8 | 30.2 | 13.087 | 0.002 | 0.382 | 0.049 | 0.017 | 0.022 | 374.220 | 0.130 | 374.8 | SIDE DRAW TO C3H6 DEGASSING |
| | | 13.104 | 0.002 | 0.366 | 0.002 | 0.000 | 0.009 | 374.218 | 0.034 | 374.6 | FROM DEGASSER TO C3H6 REGEN. |
| | | 13.435 | 0.001 | 0.037 | 0.000 | 0.000 | 0.000 | 373.191 | 0.002 | 373.2 | LIQUID FROM C3H6 REGEN. |
| 9 | 30.3 | 12.967 | 0.007 | 0.499 | 0.040 | 0.013 | 0.015 | 373.197 | 0.041 | 373.8 | |
| 10 | 30.5 | 12.538 | 0.034 | 0.901 | 0.036 | 0.013 | 0.016 | 373.201 | 0.068 | 374.3 | |
| 11 | 30.7 | 12.202 | 0.124 | 1.147 | 0.032 | 0.011 | 0.015 | 373.204 | 0.080 | 374.6 | |
| 12 | 30.9 | 11.856 | 0.397 | 1.219 | 0.029 | 0.010 | 0.013 | 373.208 | 0.080 | 375.0 | |
| 13 | 31.2 | 11.277 | 1.087 | 1.107 | 0.026 | 0.009 | 0.011 | 373.201 | 0.072 | 375.5 | |
| 14 | 31.8 | 10.316 | 2.341 | 0.814 | 0.022 | 0.008 | 0.009 | 373.212 | 0.056 | 376.5 | |
| 15 | 32.3 | 9.255 | 3.737 | 0.483 | 0.017 | 0.006 | 0.007 | 373.181 | 0.038 | 377.5 | |
| | | | | | 0.017 | 0.006 | 0.007 | | 0.038 | | DECANTED OILY PRODUCT |
| 16 | 33.5 | 7.071 | 6.095 | 0.316 | 0.000 | 0.000 | 0.000 | 373.190 | 0.000 | 379.6 | |
| 17 | 33.7 | 6.833 | 6.523 | 0.112 | 0.000 | 0.000 | 0.000 | 373.179 | 0.000 | 379.8 | |
| 18 | 33.7 | 6.809 | 6.622 | 0.037 | 0.000 | 0.000 | 0.000 | 373.180 | 0.000 | 379.8 | |
| 19 | 33.7 | 6.782 | 6.678 | 0.012 | 0.000 | 0.000 | 0.000 | 373.181 | 0.000 | 379.9 | |
| 20 | 34.2 | 6.862 | 6.607 | 0.004 | 0.000 | 0.000 | 0.000 | 373.477 | 0.000 | 380.1 | LIQUID TO REBOILER |
| | | 12.196 | 1.275 | 0.000 | 0.000 | 0.000 | 0.000 | 373.123 | 0.000 | 374.4 | LIQUID FROM REBOILER |
| | | 12.196 | 1.275 | 0.000 | 0.000 | 0.000 | 0.000 | 373.123 | 0.000 | 374.4 | LIQUID TO C2H4 RECOVERY |
| 1 | 91.8 | 13.444 | 0.028 | 0.000 | 0.000 | 0.000 | 0.000 | 369.812 | 0.00 | 369.8 | |
| 2 | 95.5 | 13.459 | 0.013 | 0.000 | 0.000 | 0.000 | 0.000 | 374.544 | 0.000 | 374.6 | |
| 3 | 99.4 | 13.472 | 0.000 | 0.000 | 0.000 | 0.000 | 0.000 | 369.652 | 0.000 | 369.7 | COMPLEXING SOLN. RECYCLE |

Others is (Ethane + methane + hydrogen);
C2H4 is ethylene;
C3H6 is propylene;
C3H8 is propane;
C4H10 is butane;
C5H12 is pentane; and
Regen. is regenerator.

We claim:

1. A process for recovering ethylene and propylene from a gaseous mixture comprising ethylene, propylene, saturated hydrocarbons and optionally other olefins which process comprises:
 (a) feeding the gaseous mixture to a separation zone comprising in its vertical orientation a top and a bottom;
 (b) feeding to the top of the separation zone at a point above the feed point of the gaseous mixture an aqueous complexing solution comprising a copper (I) salt and an aqueous solvent to form copper (I) complexes of ethylene and propylene;
 (c) feeding to the separation zone at a point below the feed point of the gaseous mixture a stripping gas comprising ethylene to strip propylene from the copper (I) complex of propylene in the separation zone;
 (d) removing from the bottom of the separation zone below the feed point of the stripping gas a first liquid stream comprising complexing solution and copper (I) complex of ethylene;
 (e) recovering ethylene from the first liquid stream by subjecting said stream to conditions of reduced pressure and/or elevated temperature;
 (f) removing from the separation zone at a point between the feed points of the gaseous mixture and the complexing solution, a second liquid stream comprising complexing solution and copper (I) complex of propylene;
 (g) recovering propylene from the second liquid stream by subjecting said stream to conditions of reduced pressure and/or elevated temperature and producing a liquid recycle stream comprising copper (I) salt; and
 (h) recycling the liquid recycle stream from step (g) to the separation zone.

2. A process according to claim 1 wherein at least part of the ethylene recovered from the first liquid stream is recycled to the stripping gas fed to the separation zone.

3. A process according to claim 1 wherein the aqueous solvent for the copper (I) salt comprise water and an organic nitrogen compound selected from the group consisting of pyridine, piperidine, hydroxypropionitrile, diethylene triamine, acetonitrile, formamide, acetamide, and derivatives thereof.

4. A process according to claim 1 wherein the copper (I) salt used in the aqueous complexing solution is selected from the group consisting of copper (I) acetate, copper (I) nitrate and copper (I) sulphate.

5. A process according to claim 1 wherein the aqueous complexing solution comprises copper (I) nitrate and hydroxypropionitrile or pyridine in a molar ratio of copper (I) salt to the nitrogen compound in the range 1:1 to 1:6.

6. A process according to claim 1 wherein the concentration of copper (I) salt in the aqueous complexing solution is at least 0.5 moles of salt per liter of solvent.

7. A process according to claim 1 wherein the gaseous mixture is treated prior to contact with the complexing solution to reduce the amount of acetylenic hydrocarbons present therein to below 20 ppm.

8. A process according to claim 7 wherein the amount of acetylenic hydrocarbons in the gaseous mixture is reduced to below 20 ppm prior to contact with the complexing solution either by absorption using a zeolite bed containing silver ions, or, by selective hydrogenation of the acetylenic hydrocarbons.

9. A process according to claim 1 wherein any hydrogen sulphide present in the gaseous mixture is removed therefrom prior to contact with the complexing solution.

10. A process according to claim 1 wherein the gaseous mixture used in the process of the present invention comprises a cracked gas from which the majority of the C5 and above hydrocarbons have been removed.

11. A process according to claim 1 wherein the gaseous mixture comprises one or more of ethylene, propylene, butenes, pentenes, methane, ethane, propane, butane, pentanes, carbon monoxide, water and hydrogen.

12. A process according to claim 1 wherein the feed of stripping gas comprising ethylene to the separation zone is controlled so that propylene is kept out of the first liquid stream removed from the separation zone.

13. A process according to claim 1 wherein the feed of complexing solution to the separation zone is controlled to keep ethylene out of the second liquid stream removed from the separation zone.

14. A process according to claim 1 wherein in step (e) the first liquid stream removed from the separation zone which comprises copper (I) complex of ethylene is subjected to conditions of temperature or pressure to recover at least a portion of the ethylene complexed with copper (I) and recycling the ethylene so recovered to the separation zone as all or part of the stripping gas.

* * * * *